United States Patent [19]

Kugele et al.

[11] E Re. 30,810

[45] Reissued Dec. 1, 1981

[54] CARBOFUNCTIONAL SULFUR AND CARBOXYLATE BRIDGED TIN COMPOUNDS

[75] Inventors: Thomas G. Kugele; Arthur F. Koeniger, both of Cincinnati, Ohio

[73] Assignees: Thiokol Corporation; Carstab Corporation, both of Reading, Ohio

[21] Appl. No.: 141,912

[22] Filed: Apr. 21, 1980

Related U.S. Patent Documents

Reissue of:

[64] Patent No.: Re. 30,032
Issued: Jun. 12, 1979
Appl. No.: 940,450
Filed: Sep. 7, 1978

Which Is a Reissue of:

[64] Patent No.: 3,979,359
Issued: Sep. 7, 1976
Appl. No.: 524,271
Filed: Nov. 15, 1974

[51] Int. Cl.[3] ..... C07F 7/22

[52] U.S. Cl. ..... 260/429.7; 260/45.75 S; 260/410.6

[58] Field of Search ..... 260/429.7

[56] References Cited

U.S. PATENT DOCUMENTS

| | | | |
|---|---|---|---|
| Re. 30,032 | 6/1979 | Kugele et al. | 260/429.7 X |
| 2,731,482 | 1/1956 | Stefl | 260/429.7 |
| 2,731,484 | 1/1956 | Best | 260/429.7 |
| 2,809,956 | 10/1957 | Mack et al. | 260/429.7 X |
| 3,478,071 | 11/1969 | Weisfeld | 260/429.7 |
| 3,565,930 | 2/1971 | Kauder et al. | 260/429.7 |
| 3,565,931 | 2/1971 | Brecker | 260/429.7 |
| 3,651,015 | 3/1972 | Ishida et al. | 260/429.7 X |
| 3,669,995 | 6/1972 | Fath et al. | 260/429.7 X |
| 3,758,341 | 9/1973 | Wowk | 260/429.7 |
| 3,758,537 | 9/1973 | Wowk | 260/429.7 |
| 3,759,966 | 7/1973 | Morton et al. | 260/429.7 |
| 3,775,451 | 11/1973 | Brecker | 260/429.7 |
| 3,778,456 | 12/1973 | Hoye et al. | 260/429.7 |
| 3,818,062 | 6/1974 | Bakassian | 260/429.7 |
| 3,819,673 | 6/1974 | Sagi et al. | 260/429.7 X |
| 3,869,487 | 3/1974 | Kugele et al. | 260/429.7 |
| 3,979,359 | 9/1976 | Kugele et al. | 260/429.7 X |
| 4,062,881 | 12/1977 | Kugele | 260/399 |

OTHER PUBLICATIONS

Sawyer, Organotin Compounds, Marcel Dekker, Inc. N.Y. vol. 2, pp. 383 to 386, 399, 401, 405, 406, 450, 452, 453 (1971).

*Primary Examiner*—Helen M. S. Sneed
*Attorney, Agent, or Firm*—Cushman, Darby & Cushman

[57] ABSTRACT

Organotin compounds are prepared having (1) at least two tin atoms linked by a bridge through sulfur, carboxylate or both and containing at least two carbon atoms in the bridge, (2) directly attached to the tin atoms one to two alkyl groups containing one to eight carbon atoms and (3) a mercaptoalkanol or derivative thereof. The compounds are useful to stabilize halogen containing vinyl and vinylidene polymers, e.g. polyvinyl chloride.

54 Claims, No Drawings

CARBOFUNCTIONAL SULFUR AND CARBOXYLATE BRIDGED TIN COMPOUNDS

Matter enclosed in heavy brackets [ ] appears in the original patent but forms no part of the first and this reissue specification; matter printed in italics indicates the additions made by the first reissue. Matter enclosed in double heavy brackets [[ ]] appears in the first reissue patent but forms no part of this reissue specification; matter printed in bold face indicates the additions made by this reissue.

The present invention relates to novel sulfur containing organotin compounds useful as stabilizers for polyvinyl chloride and other halogen containing polymers.

In the broadest aspect these are prepared organotin compounds having (1) at least two tin atoms linked by a bridge through sulfur, carboxylate groups or both, said bridge also containing at least two carbon atoms, (2) directly attached to the tin atoms one to two alkyl groups containing one to eight carbon atoms and (3) a mercaptoalkanol or derivative thereof directly attached to at least one of the tin atoms through the sulfur atom.

The bridges can be described as consisting of —S~S—, and no other functions, e.g. there are no bis oxide, alcoholate or phenate groups in the bridge. The nature of the bridge is inconsequential so long as it contains at least two carbon atoms in the chain. The requisite chain carbon atoms may or may not include the carboxylate carbon atom or atoms.

The structure can thus be

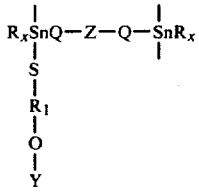

where Q is —S— or

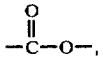

Z is any divalent organic radical which together with Q contains at least two carbon atoms, i.e. if both Q groups are —S— then Z must have at least two carbon atoms, if one Q is

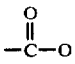

then Z must contain at least one carbon atoms and if both Q groups are

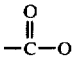

then Z may be zero (although Z can also contain one or more carbon atoms in this case also);

R is alkyl of 1 to 8 carbon atoms, x is 1 or 2 and the two x's can be the same or different.

$R_1$ can be alkylene, arylene or substituted alkylene or arylene (preferably $R_1$ is unsubstituted alkylene or arylene), Y is hydrogen, acyl, e.g. acyl of a carboxylic acid, or anything else.

In a more specific form of the invention the compounds have the formula:

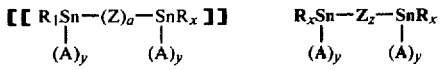

where R is a monovalent alkyl radical of 1 to 8 carbon atoms, A is

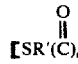

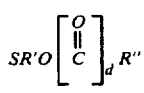

X where X is halogen of atomic weight 35 to 127, i.e., chlorine, bromine or iodine,

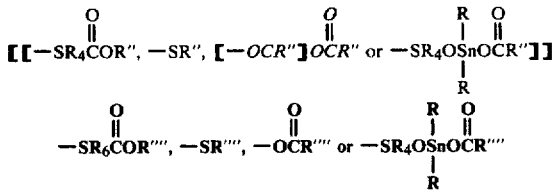

with the proviso that at least one

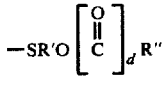

is in the molecule, d is 0 or 1, each R′ when d is 0 is alkylene of 1 to 10 carbon atoms; each R′ when d is 1 is alkylene of 2 to 10 carbon atoms, each R″ when d is 1 is alkyl of 1 to 20, preferably 1 to 18, carbon atoms, ethylenically unsaturated aliphatic hydrocarbyl having 1 to 3 ethylenic double bonds and 2 to 19, preferably 2 to 17, carbon atoms, halo or hydroxy alkyl or alkenyl of 2 to 19, preferably 2 to 17 carbon atoms, cycloalkyl of 5 to 6 carbon atoms, benzyl, phenyl, halophenyl, e.g., fluorophenyl, chlorophenyl or bromophenyl, alkylphenyl,

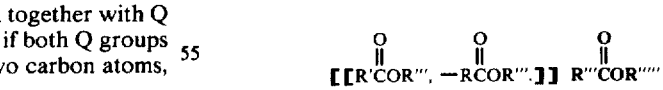

[[—R″OR″SnR$_x$]] where [[R‴]] R⁗ is alkyl [[or]] of 1 to 20, preferably 1 to 18 carbon atoms, alkenyl [[or]] of 2 to 18 carbon atoms, halo or hydroxy alkyl or alkenyl or 2 to 18 carbon atoms, cycloalkyl, of 5 to 6 carbon atoms, benzyl, phenyl, halophenyl, e.g., fluorophenyl, chlorophenyl or bromophenyl; R″ when d is 0 is hydrogen, alkyl of 1 to 20, preferably 1 to 18 carbon atoms, ethylenically unsaturated aliphatic hydrocarbyl having 1 to 3 ethylenic double bonds and 2 to 19, preferably 2 to 18 carbon atoms, cycloalkyl of 5 to 6 carbon atoms, benzyl, phenyl or halophenyl, e.g., fluorophenyl, bromophenyl or chlorophenyl, x is 1 or 2, y is 1 or 2 and z is 1 or 2, the total of x+y+z is 4, preferably x and z are 1 and y is 2, secondarily x is 2 and y and z are 1, R''' is alkylene of 2 to 10 carbon atoms, R'''' is alkyl of 1 to 20 carbon atoms, alkenyl of 2 to 18 carbon atoms, halo or hydroxy alkyl or alkenyl of 2 to 18 carbon atoms, cycloalkyl of 5 to 6 carbon atoms, benzyl, phenyl or halophenyl.

$$[Z \text{ is } -S-R_4O\overset{\overset{\displaystyle O}{\|}}{C}R_4S-]\ Z \text{ is } -S-R_4O\overset{\overset{\displaystyle O}{\|}}{C}R_4S-,$$

$$-SR_4O\overset{\overset{\displaystyle O}{\|}}{C}R_4C\overset{\overset{\displaystyle O}{\|}}{O}R_4S-,\ [[-SR_4C\overset{\overset{\displaystyle O}{\|}}{O}R_5O\overset{\overset{\displaystyle O}{\|}}{C}R_4S-,]]$$

$$-SR_6\overset{\overset{\displaystyle O}{\|}}{C}OR_{13}O\overset{\overset{\displaystyle O}{\|}}{C}R_6S-,-SR_4\overset{\overset{\displaystyle O}{\|}}{C}O,\ -O\overset{\overset{\displaystyle O}{\|}}{C}R_5\overset{\overset{\displaystyle O}{\|}}{C}O,\ -S-R_4S-,$$

$$-SR_4O\overset{\overset{\displaystyle O}{\|}}{C}R_5\overset{\overset{\displaystyle O}{\|}}{C}-O-,\ O\overset{\overset{\displaystyle O}{\|}}{C}R_5COOR_4O\overset{\overset{\displaystyle O}{\|}}{C}R_5\overset{\overset{\displaystyle O}{\|}}{C}O-$$

$$-SR_4O\overset{\overset{\displaystyle O}{\|}}{C}-R_5-\overset{\overset{\displaystyle O}{\|}}{C}-OR_4S-,$$

$$-S(CH_2)_n\overset{\overset{\displaystyle O}{\|}}{O}CCH{=}CHC\overset{\overset{\displaystyle O}{\|}}{O}(CH_2)_nS-,$$

$$[[-S(CH_2)_nC\overset{\overset{\displaystyle O}{\|}}{O}R_5O\overset{\overset{\displaystyle O}{\|}}{C}(CH_2)_nS-]] \text{ or}$$

$$-O\overset{\overset{\displaystyle O}{\|}}{C}R_9-\overset{\overset{\displaystyle O}{\|}}{C}-OR_{10}O\overset{\overset{\displaystyle O}{\|}}{C}R_9C\overset{\overset{\displaystyle O}{\|}}{O}-,\ -S(CH_2)_nC\overset{\overset{\displaystyle O}{\|}}{O}R_8O\overset{\overset{\displaystyle O}{\|}}{C}(CH_2)_nS-$$

where $R_4$ is alkylene of 2 to 10 carbon atoms, —CH=CH—, arylene (preferably phenylene,

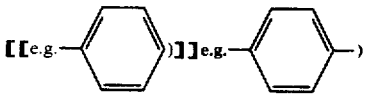

n is 1 or 2, $R_5$ is nothing, phenylene (e.g. from terephthalic acid), alkylene of 1 to 8 carbon atoms or —CH=CH—, $R_6$ is alkylene of 1 to 10 carbon atoms, —CH=CH—, arylene (preferably phenylene) or, $R_8$ is a residue of a diol, e.g. atoms the residue of a glycol such as alkylene of 2 to 10 carbon atoms, cyclohexane dimethylene, etc., $R_9$ is a residue of a dicarboxylic acid, e.g. [[—$(CH_2)$]] —$(CH_2-_m$ where m is an integer from 0 to 8, —CH=CH—, or phenylene, (particularly here the free bonds are in the para position), $R_{13}$ is phenylene, alkylene of 2 to 8 carbon atoms or —CH=CH—, $R_{10}$ is arylene, e.g. phenylene or

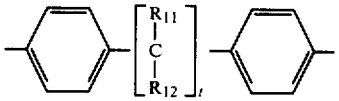

where t is 0 to 1 and $R_{11}$ and $R_{12}$ are hydrogen or alkyl, preferably t is 1 and $R_{11}$ and $R_{12}$ are both methyl, and compounds prepared by reacting a dialkytin oxide or alkyl stannoic acid with a compound of the formula.

$$[[R_x\underset{\underset{\displaystyle (A)_y}{|}}{Sn}-(Z)_x-\underset{\underset{\displaystyle (A)_y}{|}}{Sn}-[R]R_x]]$$

The grouping $$R_x\underset{\underset{\displaystyle ((A)_y}{|}}{Sn}-(Z)_z-\underset{\underset{\displaystyle (A)_y}{|}}{Sn}-[R]R_x$$

$$-SCH_2CH_2O\overset{\overset{\displaystyle O}{\|}}{C}CH{=}CH\overset{\overset{\displaystyle O}{\|}}{C}OCH_2CH_2S-$$

can be formed by reacting two moles of mercaptoethanol and one mole of maleic acid. The grouping $$[[-S(CH_2)_nC\overset{\overset{\displaystyle O}{\|}}{O}R_xO\overset{\overset{\displaystyle O}{\|}}{C}(CH_2)nS]]$$

$$-S(CH_2)_nC\overset{\overset{\displaystyle O}{\|}}{O}R_8O\overset{\overset{\displaystyle O}{\|}}{C}(CH_2)_nS$$

can be formed by reacting two moles of thioglycolic acid or beta thiopropionic acid with one mole of a diol, e.g. ethylene glycol, diethylene glycol, propylene glycol, decamethylene glycol. The grouping $$O\overset{\overset{\displaystyle O}{\|}}{C}R_9-\overset{\overset{\displaystyle O}{\|}}{C}-OR_{10}-O\overset{\overset{\displaystyle O}{\|}}{C}R_9\overset{\overset{\displaystyle O}{\|}}{C}-O$$

can be formed by reacting two moles of a dicarboxylic acid, e.g. maleic acid, oxalic acid, succinic acid, adipic acid, terephthalic acid with one mole of a dihydric phenol, e.g. hydroquinone or a bisphenol, e.g. 4,4'-dihydroxydiphenyl, p,p'-diphenylolpropane (bisphenol A), bis (4-hydroxyphenyl) methane, etc.

The compounds are useful to stabilize halogen containing vinyl and vinylidene resins, e.g. polyvinyl chloride.

Examples of groups within R are methyl, ethyl, propyl, isopropyl, n-butyl, isobutyl, sec. butyl, t-butyl, amyl, hexyl, octyl, 2-ethylhexyl and isoctyl. Most preferably R is methyl. Examples of subgroups within R are (a) methyl and butyl and (b) methyl, butyl and octyl.

When A is halogen it is preferably chlorine.

Examples of R' (and also of $R_6$) groups are methylene, ethylene, propylene, trimethylene, tetramethylene, pentamethylene, octamethylene, hexamethylene, decamethylene, p-phenylene and m-phenylene. Examples of $R_4$ are the same as those mentioned for R' except that methylene is omitted. Examples of $R_5$ are nothing, methylene, ethylene, trimethylene, propylene, tetramethylene, pentamethylene, hexamethylene, octamethylene, —CH=CH— (either cis or trans).

The compounds of the present invention can be made in various ways such as those illustrated below, for example.

Conveniently, the tin is added as the monoalkyltin trihalide, e.g., methyltin trichloride, methyltin tribromide, methyltin triiodide, ethyltin trichloride, sec. butyltin trichloride, butyltin tribromide or octyltin trichloride, the dialkyltin dihalide, e.g., dimethyltin dichloride, dimethyltin dibromide, dimethyltin diiodide, dipropyltin dichloride.

When monomethyltin and dimethyltin halides or other mono or dimethyltin starting compounds are used in order to insure low toxicity, the amount of tin present as trimethyltin compound impurity should be less than 0.5%.

The $$-SR'O\left[\overset{O}{\overset{\|}{C}}\right]_d R''$$

grouping can be attached to the tin by reacting the above mentioned mono or dialkyltin halides with a compound having the formula $$[[HSR'O\overset{O}{\overset{\|}{(C)}}_eR'']]\ HSR'O\left[\overset{O}{\overset{\|}{C}}\right]_dR''$$

Thus there can be employed mercaptoalkanol esters, for example, esters of mercaptoethanol, 2-thioglycerine, 3-thioglycerine, 3-thiopropanol, 2-thiopropanol, 4-thiobutanol, 18-thio-octadecanol, 9-thiononanol, 8-thiooctanol, 6-thiohexanol with acids such as formic acid, acetic acid, propionic acid, butyric acid, pivalic acid, valeric acid, caprylic acid, caproic acid, decanoic acid, lauric acid, myristic acid, palmitic acid, 2-ethylhexanoic acid, stearic acid, eicosanic acid, oleic acid, linoleic acid, linolenic acid, crotonic acid, methacrylic acid, acrylic acid, cinnamic acid, benzoic acid, p-toluic acid, o-toluic acid, p-t-butyl-benzoic acid, enanthic acid, p-n-butylbenzoic acid, cyclohexane carboxylic acid, phenylacetic acid, ricinoleic acid, hydrogenated ricinoleic acid, phenylpropionic acid. Of course, mixtures of acids can be used, e.g., tall oil acids, palmitic acid-stearic acid mixtures ranging from 60:40 to 40:60; soybean oil acids, cottonseed oil acids, hydrogenated cottonseed oil acids, peanut oil acids, coconut oil acids, corn oil acids, castor oil acids, hydrogenated castor oil acids, lard acids, etc. Illustrative of half esters of polycarboxylic acids which can be esterified with the mercaptoalkanol are mono methyl maleate, monoethyl maleate, monopropyl maleate, monobutyl maleate, monooctyl maleate, mono-2-ethylhexyl maleate, mono stearyl maleate, monoethyl fumarate, monomethyl oxalate, monoethyl oxalate, monoethyl malonate, monobutyl malonate, monoisopropyl succinate, monomethyl succinate, monomethyl glutarate, monoethyl adipate, monomethyl azelate, monomethyl phthalate, monoethyl phthalate, monoisooctyl phthalate, monoethyl terephthalate.

Illustrative of mercapto esters which can be used for reaction with the tin compound are:

2-mercaptoethyl acetate,
2-mercaptoethyl propionate,
2-mercaptoethyl butyrate,
2-mercaptoethyl valerate,
2-mercaptoethyl pivalate,
2-mercaptoethyl caproate,
2-mercaptoethyl caprylate,
[2pelargonate, pelargonte] *2-mercaptoethyl pelargonate,*
2-mercaptoethyl decanoate,
2-mercaptoethyl laurate,
2-mercaptoethyl stearate,
2-mercaptoethyl eicosanate,
2-mercaptoethyl palmitate,
2-mercaptoethyl oleate,
2-mercaptoethyl ricinoleate,
2-mercaptoethyl linoleate,
2-mercaptoethyl linolenate,
2-mercaptoethyl tallate,
2-mercaptoethyl ester of cottonseed oil acid,
2-mercaptoethyl ester of lard acids,
2-mercaptoethyl ester of coconut oil acids,
2-mercaptoethyl ester of soybean oil acids,
2-mercaptoethyl benzoate,
2-mercaptoethyl p-toluate,
2-mercaptoethyl crotonate,
2-mercaptoethyl cinnamte,
2-mercaptoethyl phenyl acetate,
2-mercaptoethyl phenyl propionate,
2-mercaptoethyl methyl maleate,
2-mercaptoethyl ethyl fumarate,
2-mercaptoethyl butyl oxalate,
2-mercaptoethyl methyl oxalate,
2-mercaptoethyl ethyl malonate,
2-mercaptoethyl methyl succinate,
2-mercaptoethyl methyl azelate,
2-mercaptoethyl hexyl azelate,
2-mercaptoethyl methyl phthalate,
3-mercaptopropyl pelargonate,
3-mercaptopropyl enanthate,
3-mercaptopropyl stearate,
3-mercaptopropyl oleate,
3-mercaptopropyl ricinoleate,
3-mercaptopropyl ethyl maleate,
3-mercaptopropyl benzoate,
2-thioglyceryl pelargonate,
3-thioglyceryl pelargonate, 2-mercaptoethyl-bromoacetate,
6-mercaptohexyl acetate, 2-mercaptoethyl-3'-fluorobenzoate,
7-mercaptoheptyl acetate, 2-mercaptoethyl-2'-bromobenzoate,
7-mercaptoheptyl propionate, 2-mercaptoethyl-4'-chlorobenzoate,
8-mercaptooctyl acetate, 2-mercaptoethyl-2'-chloropropionate,
8-mercaptooctyl enanthate, 2-mercaptoethyl chloroacetate,
18-mercaptooctadecyl acetate, 2-mercaptoethyl trichloroacetate,
18-mercaptooctadecyl enanthate, 2-mercaptoethyl cyclohexanoate,
2-mercaptoethyl cyclopentanoate.

When d is zero sulfur compounds employed include thioalkanols such as 2-mercaptoethanol, 3-mercaptopropanol, 4-mercaptobutanol, 3-mercaptobutanol, 5-mercaptopentanol, 10-mercaptodecanol.

Additional starting compounds of the formula $$HSR'O\overset{O}{\overset{\|}{C}}R''$$

include monothioglycerine dicaprylate, monothioglycerine diacetate, monothioglycerine distearate, monothioglycerine dioleate, monothioglycerine dilinoleate.

The Z linkage in the compounds except when Z is —O— can be formed by reacting a compound of the formula HZH with a compound of the formula:

$$R_xSn-Hal\ (SR'O\overset{O}{\overset{\|}{(C)}}_dR'')_y$$

where Hal is a halogen, e.g., chlorine, bromide or iodine. Examples of compounds having the formula HZH are mercaptoethylmercaptopropionate, mercaptoethylthioglycolate, 3-mercaptopropylthioglycolate, 3-mercaptopropyl mercaptopropionate, mercaptoethylmercapto-butyrate, mercaptoethyl mercaptodecanoate, 10-mercaptodecylthioglycolate, 4-mercaptobutylmercaptopropionate, mercaptoethylthioglycolic acid mercaptoethyl ester, mercaptopropyl-thioglycolic acid mercaptoethyl ester, mercaptoethylthiogylcolic acid, mercaptopropyl ester, mercaptoethylmercaptopropionic acid mercaptoethyl ester, mercaptopropylmercaptopropionic acid mercaptopropyl ester, bis(2-mercaptoethyl-)adipate, bis(3-mercaptopropyl adipate) bis(4-mercaptobutyl)adipate, bis(10-mercapto-decyl)adipate, bis(2-mercaptoethyl)maleate, bis(3-mercaptopropyl)maleate, bis(2-mercaptopropyl)adipate, bis(4-mercaptobutyl)-maleate, bis(2-mercaptoethyl)furmarate, bis(3-mercaptopropyl)fumarate, bis(2-mercaptoethyl)oxalate, bis(3-mercaptopropyl)malonate, bis(2-mercaptoethyl)succinate, bis(3-mercaptopropyl) succinte, bis(2-mercaptoethyl) glutarate, bis(3-mercaptopropyl) azelate, bis(2-mercaptoethyl)suberate, bis(2-mercaptoethyl)sebacate, bis(2-mercaptoethyl) terephthalate, thioglycolic acid, alpha mercapto propionic acid, beta mercaptopropionic acid, alpha mercaptobutyric acid, gamma mercaptobutyric acid, oxalic acid, malonic acid, adipic acid, succinic acid glutaric acid, azelaic acid, sebacic acid, ethanedithiol, propanedithiol-1,3, butanedithiol-1,4, butanedithiol-1,3 hexanedithiol-1,6, decanedithiol-1,10, mercaptoethanol, 3-mercaptopropanol, 4-mercaptobutanol, mono-mercaptoethyl maleate, mono-mercaptoethyl fumarate, mono-mercaptoethyl adipate, monomercaptopropyl adipate, mono-mercaptoethyl terephthalate, bis(2-mercaptoethyl) maleate, mono-mercaptoethyl, sebacate, mono-mercaptoethyl succinate, tetramethylene glycol bis maleate, tetramethylene glycol bis fumarate, tetramethylene glycol bis succinate, tetramethylene glycol bis sebacate, tetramethylene glycol bis oxalate, ethylene glycol bis terepthalate, tetramethylene glycol bis(mercaptoacetate), ethylene glycol bis maleate, ethylene glycol bis fumarate, propylene glycol bis(3-mercaptopropionate), bisphenol A bis(-maleate), ethylene glycol bis adipate, ethyleneglycol bis glutarate, bisphenol A bis(terepthalate), bisphenol A bis(adipate), propylene glycol bis maleate, propylene glycol bis adipate, trimethylene glycol bis adipate, hexamethylene glycol bis adipate, hexamethylene glycol bis maleate, decamethylene glycol bis adipate, decamethylene glycol bis maleate.

When Z is —O— the products of the invention can be prepared by reacting either an alkyl halotin dihydroxide, e.g., methyl chlorotin dihydroxide, butyl chlorotin dihydroxide, octylchlorotin dihydroxide, methyl bromotin dihydroxide or an alkyl stannoic acid, e.g., methyl stannoic acid, butylstannoic acid, octylstannoic acid with a compound of the formula:

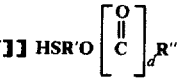

In addition to the group of compounds set forth above, there can also be employed overbased tin compounds by reacting a dialkyltin oxide of the formula

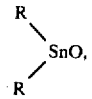

dimethyltin oxide, dibutyltin oxide, or dioctyltin oxide, or an alkylstannoic acid RSnOOH, e.g., methylstannoic acid, butylstannoic acid or octylstannoic acid with a compound of the invention of the formula:

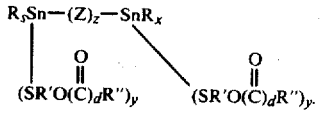

There can be used up to 2 moles, e.g., 0.1 to 2 moles of dialkyltin oxide or alkylstannoic acid per ester group of the sulfur containing compounds.

The overbased product has the same uses as the other products of the invention. It is particularly surprising that overbased products can be made with dimethyltin oxide since while it is not soluble in many other materials, it is soluble in the compounds of the invention.

The overbasing reaction is further shown in Weisfeld U.S. Pat. No. 3,478,071 and Stapfer et al, J. Organometallic Chemistry Vol. 24 (1970) pages 355-358. The entire disclosures of the Weisfeld patent and Stapfer article are hereby incorporated by reference.

In preparing the compounds of the invention, various processes can be employed some of which are illustrated in the working examples. Regardless, however, of the method employed, the reaction can be carried out at a wide range of temperatures, e.g., room temperature to 100° C. usually at 25°-50° C. The reaction is usually carried out with water as a solvent, regardless of the procedure employed. There can also be employed water immiscible organic solvents, e.g., aliphatic and aromatic hydrocarbons, e.g., hexane, octane, benzene, toluene, xylene, aliphatic carboxylic Acid esters, e.g., butyl acetate, propyl propionate, methyl valerate. The proportions of solvent are not critical and can vary widely.

Unless otherwise indicated, all parts and percentages are by weight.

In the examples, the refractive indices (R.I.) were measured at 25° C. unless otherwise indicated.

EXAMPLE 1

Into a 3-necked flask is placed 120 gm (0.5 mole) of methyltintrichloride dissolved in 200 ml of water. The mixture is [[armed]] warmed to 30° C., and there is added 204 gm (1.0 mole) of 2-mercaptoethyl caprylate. Then there is added dropwise at 30° C. 80 gm (1.0 mole) of 50% aqueous sodium hydroxide. The mixture is stirred for 1 hour at 30°-40° C. After this reaction time, 66.5 gm (0.25 mole) of bis(2-mercaptoethyl) adipate is added portionwise followed by 40 g (0.5 mole) of 50% NaOH and the mixture allowed to stir 1 hour at 30°-40° C. The product layer is separated and washed with 200 ml of water. The product is then stripped under vacuum to 100° C. resulting in 318 gm. of a nearly colorless oil. The product is mainly bis(methyltin bis[2-mercaptoethyl caprylate]-mercaptoethyl)adipate, $n_D^{25}$ *1.5283*

EXAMPLE 2

The procedure of Example 1 was followed replacing the bis(2-mercaptoethyl)adipate with 42 gm (0.25 mole) of mercaptoethylmercaptopropionate. Obtained is 295 gm of a pale yellow oil, bis(methyltin bis[2-mercaptoethylcaprylate])mercaptoethylmercaptopropionate, [$D^{25}$] $n_D^{25}$ 1.5352.

EXAMPLE 3

The procedure of Example 1 was followed replacing the bis(2-mercaptoethyl)adipate with 59 gm (0.25 mole) of bis(2-mercaptoethyl)maleate. Obtained is 302 gm of a pale yellow oil, bis(methyl-tin bis[2-mercaptoethylcaprylate]mercaptoethyl) maleate. $n_D^{25}$ 1.5389.

EXAMPLE 4

The procedure of Example 1 was followed replacing the bis(2-mercaptoethyl)adipate with 52 gm (0.25 mole) of glycol bis(thioglycolate). Obtained is 299 gms of a nearly colorless oil, $n_D^{25}$ 1.5193. The product includes:

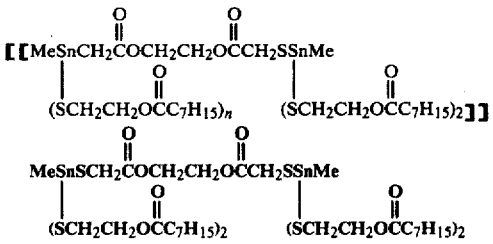

EXAMPLE 5

The procedure of Example 1 was followed replacing the bis(2-mercaptoethyl)adipate with 23 gm (0.25 mole) of thioglycolic acid. Obtained is 273 gms of a colorless oil $n_D^{25}$ 1.5404. The product includes:

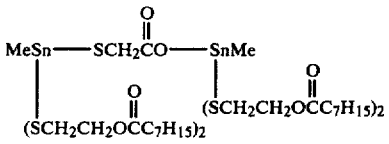

EXAMPLE 6

The procedure of Example 1 was followed replacing the bis(2-mercaptoethyl)adipate with 29 gm (0.25 mole) of maleic acid. Obtained is 276 gm of yellow oil. $n_D^{25}$ 1.5371. The product includes:

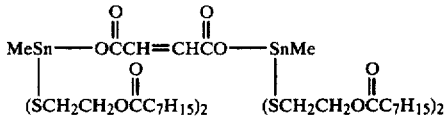

EXAMPLE 7

Into a 3-necked flask is placed 120 g (0.5 mole) of methyltintrichloride dissolved in 200 ml of water. The mixture is warmed to 30° C. and there is added 153 gm (0.75 mole) of 2-mercaptoethylcaprylate. Then there is added dropwise at 30° C., 60 gms (0.75 mole) of 50% aqueous sodium hydroxide. The mixture is stirred for 1 hour at 30°-40° C. After this reaction time 66.5 gm (0.25 mole) of bis(2-mercaptoethyl) adipate is added portionwise followed by 40 gm (0.50 mole) of 50% aqueous NaOH, and the mixture allowed to stir 1 hour at 30°-40° C. The product layer is separated and washed with 200 ml of water. The product is then stripped under reduced pressure resulting in 263 gms of colorless oil. $n_D^{25}$ 1.5396. The product includes:

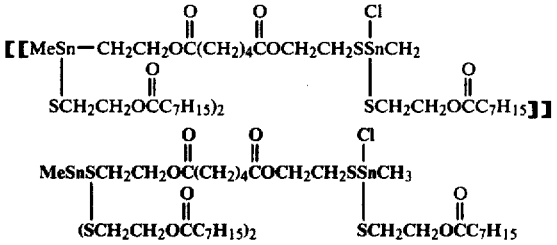

EXAMPLE 8

Into a 3-necked flask is placed 110 gm (0.5 mole) of dimethyltin dichloride dissolved in 200 ml of water. The mixture is warmed to 30° C. and there is added 170 gm (0.5 mole) 2-mercaptoethyloleate. Then there is added dropwise at 30° C., 40 gms (0.5 mole) of 50% aqueous sodium hydroxide. The mixture is stirred for 1 hour at 30°-40° C. After this reaction time, 66.5 gm (0.25 mole) of bis(2-mercaptoethyl) adipate is added, then followed closely by 40 gm (0.5 mole) of 50% aqueous NaOH then allowed to stir 1 hour at 30°-40° C. The product layer is separated and washed with 200 ml of water, then stripped under vacuum to 100° C., resulting in 296 gm of a yellow oil. $n_D^{25}$ 1.5106. The reaction product contains:

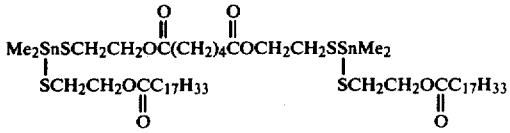

EXAMPLE 9

Into a 3-necked flask is placed 55 gms (0.25 mole) dimethyltindichloride, 60 gm (0.25 mole) of methyltin trichloride dissolved in 200 ml of water. The mixture is warmed to 30° C. and there is added 255 (0.75 mole) of 2-mercaptoethyloleate. [Then there is added dropwise at 30° C. 60 gm (0.75 mole) of 2-mercaptoethyloleate.] Then there is added dropwise at 30° C. 60 gm (0.75 mole) of 50% aqueous sodium hydroxide. The mixture is stirred for 1 hour at 30°-40° C. After this reaction time, 66.5 gm (0.25 mole) of bis(2-mercaptoethyl)adipate is added, then followed immediately by 40 gm (0.50 mole) of aqueous NaOH, then allowed to stir 1 hour at 30°-40° C. The product layer is separated, washed with 200 ml of water, then stripped under vacuum to 100° C. resulting in 383 gm of a yellow oil. $n_D^{25}$ 1.5080. The reaction product contains:

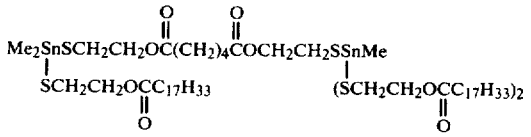

EXAMPLE 10

The procedure of Example 1 was followed replacing the bis(2-mercaptoethyl)adipate with 41.5 gm (0.25 mole) 2-mercaptoethyl maleate. Obtained are 287 gms of a pale yellow oil, $n_D^{25}$ 1.5384. The product includes:

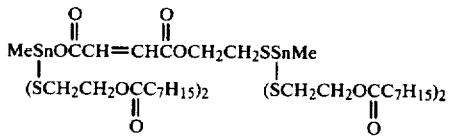

EXAMPLE 11

The procedure of Example 1 was followed replacing the 2-mercaptoethylcaprylate with 330 gm (1.0 mole) of 2-mercaptoethyloctadecylether. Obtained is 441 gm of a nearly colorless oil, containing bis(methyltin bis[2-mercaptoethyloctadecylether]-mercaptoethyl)adipate. $n_D^{25}$ 1.5149.

EXAMPLE 12

The procedure of Example 1 as followed replacing the 2-mercaptoethylcaprylate with 360 gm (0.0 mole) of monothioglycerine dicaprylate ester. Obtained is 458 gm of a yellow oil, containing bis(methyltin bis[thioglycerinedicaprylate]-2-mercapto-ethyl)adipate. $n_D^{25}$ 1.5160.

EXAMPLE 13

The procedure of Example 1 was followed replacing the bis(2-mercaptoethyl)adipate with 23.5 gm (0.25 mole) ethanedithiol. Obtained is 269 mg of a very odoriferous pale yellow oil, $n_D^{25}$ 1.5272 containing:

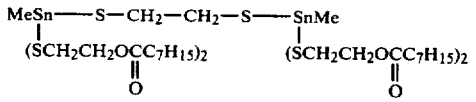

EXAMPLE 14

The procedure of Example 1 was followed replacing the 2-mercaptoethylcaprylate with 260 gm (1.0 mole) of 6-mercaptohexylcaprylate. Obtained is 366 gm of a pale yellow oil, $n_D^{25}$ 1.5202, mainly bis(methyltin bis[6-mercaptohexylcaprylate]-2-mercaptoethyl)adipate.

EXAMPLE 15

The procedure of Example 1 was followed replacing the bis(2-mercaptoethyl)adipate with 71.5 gm (0.25 mole) of tetramethylene glycol bis maleate. Obtained is 314 gm of a pale yellow oil. $n_D^{25}$ 1.5349, containing

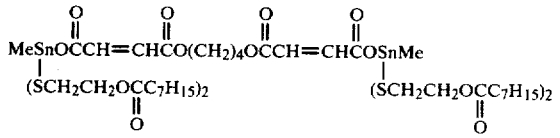

EXAMPLE 16

The procedure of Example 9 was followed replacing the bis(2-mercaptoethyl)adipate with 38 gm (0.25 mole) of mercaptoethylthioglycolate. Obtained is 342 gm of a pale yellow oil, $n_D^{25}$ 1.5161, containing:

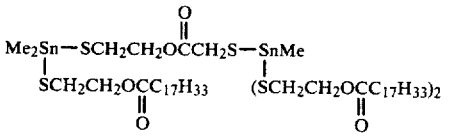

EXAMPLE 17

Into a 3-necked flask is placed 55 gm (0.25 mole) dimethyltindichloride, 60 gm (0.25 mole) methyltintrichloride dissolved in 200 ml of water. The mixture is warmed to 30° C. and there is added 102 gm (0.50 mole) of 2-mercaptoethyl caprylate. Then there is added dropwise at 30° C. 40 gm (0.5 mole) of 50% aqueous sodium hydroxide. The mixture is stirred for 1 hour at 30°-40° C. After this reaction time 42 gm (0.25 mole) of mercaptoethylmercaptopropionate is added, then followed immediately by 40 gm (0.5 mole) aqueous NaOH (50%), then allowed to stir 1 hour at 30°-40° C. The product layer is separated washed with 200 ml of water, then stripped under vacuum to 100° C. resulting in 192 gm of a yellow oil $n_D^{25}$ 1.5428 containing:

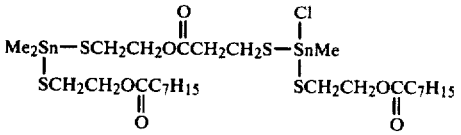

EXAMPLE 18

The procedure of Example 1 was followed replacing the monomethyltintrichloride with 141 gm (0.5 mole) of butyltintrichloride. Obtained is 330 gm of a pale yellow oil. The product is mainly bis(butyltin bis[2-mercaptoethyl caprylate]-2-mercaptoethyl)-adipate, $n_D^{25}$ 1.5210.

EXAMPLE 19

The procedure of Example 7 was followed replacing the methyltintrichloride with 141 gm (0.5 mole) of butyltintrichloride and the bis(2-mercaptoethyl)adipate with 59 gm (0.25 mole) of bis(2-mercaptoethyl)-maleate. Obtained is 280 gm of a nearly colorless oil, $n_D^{25}$ 1.5420, containing:

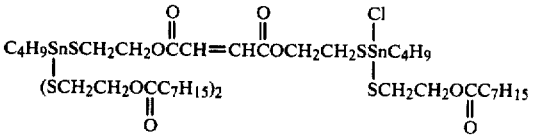

EXAMPLE 20

The procedure of Example 9 was followed, replacing the dimethyltindichloride with 75.5 gm (0.25 mole) of dibutyltindichloride, the methyltintrichloride with 70.5 gm (0.25 mole) of butyltintrichloride. Obtained is 402 gms of a yellow oil, $n_D^{25}$ 1.5077, containing:

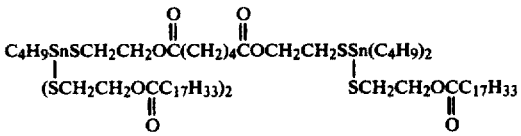

EXAMPLE 21

Into a 3-necked flask is placed 329 gm (0.25 mole) of bis(methyltin bis[2-mercaptoethyl caprylate]mercaptoethyl) adipate and 41 gm (0.25 mole) of dimethyltin oxide. The mixture is heated at 80°-120° C. over a 2-hour period, cooled to 40°-50° C. and filtered yielding 370 gms of a pale yellow oil $n_D^{25}$ 1.5303 containing:

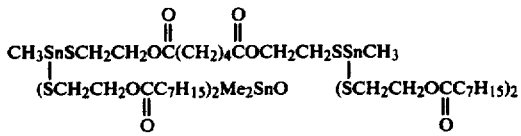

where the $Me_2SnO$ is inserted into one of the ester functions, possibly

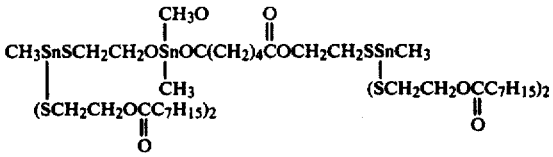

and/or

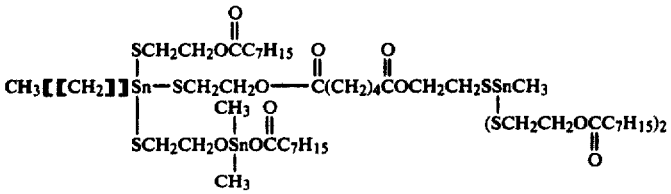

EXAMPLE 22

Into a 3-necked flask is placed 122.5 gm (0.5 mole) of "butylchlorotindihydroxide," 165 gm (0.5 mole) of 2-mercaptoethyl oleate and 750 ml of toluene. The mixture is refluxed until 8.5 ml of water are removed. The organic layer is stripped yielding 260 gm of a yellow oil. $n_D^{25}$ 1.5320. The oil contains bis(monobutylmonochlorotin[2-mercaptoethyloleate]) oxide.

EXAMPLE 23

Into a 3-necked flask is placed 113.5 gm (0.5 mole) of butylstannoic acid, 204 gm (1.0 mole) of 2-mercaptoethylcaprylate and 300 ml of toluene. The mixture is refluxed until 18.0 ml of water are removed. The organic layer is stripped yielding 290 gm of a nearly colorless oil, $n_D^{25}$ 1.5232. The oil contains bis(monobutyltin bis[2-mercaptoethylcaprylate][D]) oxide.

EXAMPLE 24

The procedure of Example 1 was followed replacing the bis(2-mercaptoethyl) adipate with 41.5 g (0.25 mole) of terephthalic acid. Obtained is 286 gm of yellow oil. $n_D^{25}$ 1.5488. The product is in part

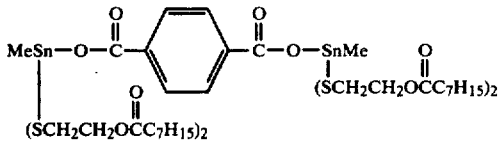

EXAMPLE 25

The procedure of Example 9 was followed replacing the bis(2-mercaptoethyl) adipate with 105 g (0.25 mole) of reaction product of bis phenol A 118 gms (0.5 mole) and 116 gms (1.0 mole) maleic acid. Obtained is 421 gm of amber oil. $n_D^{25}$ 1.5286. The reaction product contains

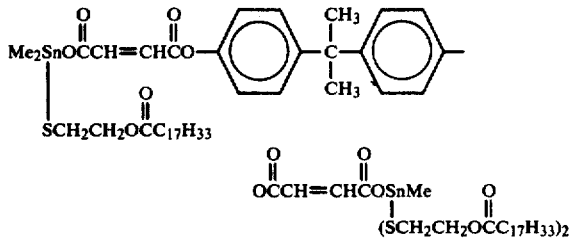

The stabilizers of the present invention can be used with halogen-containing vinyl and vinylidene polymers, e.g., resins in which the halogen is attached directly to the carbon atoms. Preferably the polymer is a vinyl halide polymer, specifically a vinyl chloride polymer. Usually, the vinyl chloride polymer is made from monomers consisting of vinyl chloride alone or a mixture of monomers comprising at least 70% vinyl chloride by weight. When vinyl chloride copolymers are stabilized, preferably the copolymer of vinyl chloride with an ethylenically unsaturated compound copolymerizable therewith contains at least 10% of polymerized vinyl chloride.

As the chlorinated polymer there can be employed chlorinated polyethylene having 14 to 75%, e.g., 27% chloride by weight, chlorinated natural and synthetic rubber, rubber hydrochloride, chlorinated polystyrene, chlorinated polyvinyl chloride, polyvinyl chloride, polyvinylidene chloride, polyvinyl bromide, polyvinyl fluoride, copolymers of vinyl chloride with 1 to 90%, preferably 1 to 30% of a copolymerizable ethylenically unsaturated material such as vinyl acetate, vinyl butyrate, vinyl benzoate, vinylidene, chloride, diethyl fumarate, diethyl maleate, other alkyl fumarates and maleates, vinyl propionate, methyl acrylate, 2-ethylhexylacrylate, butyl acrylate and other alkyl acrylates, methyl methacrylate, ethyl methacrylate, butyl methacrylate and other alkyl methacrylates, methyl alpha chloroacrylate, styrene, trichloroethylene, vinyl ethers such as vinyl ethyl ether, vinyl chloroethyl ether and vinyl phenyl ether, vinyl ketones such as vinyl methyl ketone and vinyl phenyl ketone, 1-fluoro-2-chloroethylene, acrylonitrile, chloroacrylonitrile, allylidene diacetate and chloroallyidene diacetate. Typical copolymers include vinyl chloride-vinyl acetate (96:4 sold commercially as VYNW), vinyl chloride-vinylacetate (87:13), vinyl chloride-vinyl acetate-maleic anhydride (86:13:1), vinyl chloride-vinylidene chloride (95:5), vinyl chloride-diethyl fumarate (95:5), vinyl chloride-trichloroethylene (95:5), vinyl chloride-2-ethylhexyl acrylate (80:20).

The stabilizers of the present invention can be incorporated with the polymer by admixing in an appropriate mill or mixer of by any of the other well-known methods which provide for uniform distribution throughout the polymer composition. Thus, mixing can be accomplished by milling on rolls at 100°-160° C.

In addition to the novel stabilizers, there can also be incorporated with the resin, conventional additives such as plasticizers, pigments, fillers, dyes, ultraviolet light absorbing agents, densifying agents and the like. There can also be added conventional and known tin stabilizers, e.g., those disclosed in Kauder or Kugele et al or in Weisfeld U.S. Pat. No. 3,640,950, Leistner U.S. Pat. Nos. 2,870,119 and 2,870,182, Best U.S. Pat. No. 2,731,484, Stefl U.S. Pat. No. 2,731,482, and Mack U.S. Pat. No. 2,914,506, for example. The entire disclosures of all the patents mentioned in this paragraph are hereby incorporated by reference.

If the plasticizer is employed, it is used in conventional amount, e.g., 10 to 150 parts per 100 parts of polymer. Typical plasticizers are di-2-ethylhexyl phthalate, dibutyl sebacate, dioctyl sebacate, tricresyl phosphate.

The tin containing stabilizers of the invention are normally used in an amount of 0.01 to 10% by weight of the polymer, more preferably 0.2 to 5% of the tin compound is used by weight of the polymer.

As indicated, there can also be incorporated 0.1 to 10 parts per 100 parts of the halogen containing polymer of a metal salt stabilizer. Thus, there can be used barium, strontium, calcium, cadmium, zinc, lead, tin, magnesium, cobalt, nickel, titanium and aluminum salts of phenols, aromatic carboxylic acids, fatty acids or epoxy fatty acids.

Examples of suitable salts include barium di(nonylphenolate), strontium di(nonylphenolate), strontium di(amylphenolate), barium di(octylphenolate), strontium di(octylphenolate), barium di(nonyl-o-cresolate), lead di(octylphenolate), cadmium-2-ethyl hexoate, cadmium laurate, cadmium stearate, zinc caprylate, cadmium caprate, barium stearate, barium-2-ethylhexoate, barium laurate, barium ricinoleate, lead stearate, aluminum stearate, magnesium stearate, calcium octoate, calcium stearate, cadmium naphthenate, cadmium benzoate, cadmium p-tert. butylbenzoate, barium octyl salicylate, cadmium epoxy stearate, strontium epoxy stearate, cadmium salt of epoxidized acids of soybean oil, and lead epoxy stearate.

In plastisol formulations there is preferably also included from 0.1 to 10 parts per 100 parts of polymer of an epoxy vegetable oil such as epoxidized soybean oil or epoxidized tall oil, epoxy esters of fatty acids, e.g., isooctyl epoxystearate.

EXAMPLE 26

100 Parts of a polyvinyl chloride commercially available under the trade designation Geon 103 EP are admixed with 1.0 parts Omya 90T (fine particle size $CaCO_3$ coated with Ca stearate), 1.0 part of a paraffin wax commercially available under the trade designation Advawax 165, 0.1 part AC 629A (oxidized low molecular weight ethylene homopolymer) and stabilizer as noted in Table I. The composition is heated to 380° F. and milled with sampling at 1 minute intervals after first introduction of mixture to the mill. The results of the tests are found in Table I.

TABLE 1

| Product of Example No. | Tin Contained (mg) | Dynamic Mill Stability 380° F. 30/40 RPM(minutes) | | | | | | | | | |
|---|---|---|---|---|---|---|---|---|---|---|---|
| | | 1 | 2 | 3 | 4 | 5 | 6 | 7 | 8 | 9 | 10 |
| 1 | 40 | 10 | 10 | 9 | 7+ | 6 | 5 | 4 | 2 | 2 | 2 |
| 2 | 40 | 10 | 9+ | 9 | 8 | 6 | 5 | 4 | 3 | 1 | 1 |
| 3 | 40 | 10+ | 10+ | 10 | 9 | 8 | 7+ | 5 | 3 | 2 | 2 |
| 5 | 40 | 9 | 8 | 7 | 5 | 4 | 3 | 3 | 2 | 2 | 1 |
| 7 | 40 | 9 | 8+ | 8 | 7 | 6 | 5 | 4 | 3 | 2 | 1 |
| 8 | 40 | 8+ | 8 | 7 | 6 | 5 | 4 | 4 | 3 | 2 | 2 |
| 9 | 40 | 10 | 10 | 9+ | 8+ | 7 | 6 | 5+ | 4 | 3 | 2 |
| * | 40 | 9 | 8 | 7 | 6 | 5 | 5 | 4 | 2 | 2 | 2 |

Color Scale: 10(white)-5(tan-orange)-0(burn)

*⅓ monomethyltin tris(isooctylthioglycolate) and ⅔ dimethyltin bis(isooctylthioglycolate)

As can be seen from Table I the products of the invention on the whole showed as good or better dynamic mill stability than the comparative stabilizer.

What is claimed is:

1. A sulfur containing organotin compound having the formula (1):

$$[[\,R_1Sn(A)_y-(Z)_a-SnR_x(A)_y\,]] \qquad R_xSn(A)_y-Z_z-SnR_x(A)_y$$

where R is a monovalent alkyl radical of 1 to 8 carbon atoms, A is $$-SR'O\left[\overset{O}{\overset{\|}{C}}\right]_d R'',$$

halogen of atomic weight 35 to 127, $$-SR_6\overset{O}{\overset{\|}{C}}OR'''', -SR'''', -\overset{O}{\overset{\|}{C}}OR'''' \text{ or } -SR_4O\underset{\underset{R}{|}}{\overset{\overset{R}{|}}{Sn}}\overset{O}{\overset{\|}{C}}OR'''',$$

the A groups are the same or different with the proviso that at least one $$-SR'O\left[\overset{O}{\overset{\|}{C}}\right]_d R''$$

is in the molecule, d is 0 or 1, each R′ when d is 0 is alkylene of 1 to 10 carbon atoms, each R′ when d is 1 is alkylene of 2 to 10 carbon atoms, each R″ *when d is 1* is [hydrogen,] alkyl of 1 to 20 carbon atoms, ethylenically unsaturated aliphatic hydrocarbyl having 1 to 3 ethylenic double bonds and 2 to 19 carbon atoms, halo or hydroxy alkyl of 2 to 19 carbon atoms, halo or hydroxy alkenyl of 2 to 19 *carbon atoms*, cycloalkyl of 5 to 6 carbon atoms, benzyl, phenyl, alkylphenyl, halophenyl, $$[[R'''\overset{O}{\overset{\|}{C}}OR'']] \qquad R'''\overset{O}{\overset{\|}{C}}OR''''$$

where R‴ is alkylene of 2 to 10 carbon atoms, *each R″ when d is 0 is hydrogen, alkyl of 1 to 20 carbon atoms, ethylenically unsaturaed aliphatic hydrocarbyl having 1 to 3 ethylenic double bonds and 2 to 19 carbon atoms, cycloalkyl of 5 to 6 carbon atoms, benzyl, phenyl or halophenyl,* R⁗ is alkyl of 1 to 20 carbon atoms, alkenyl of 2 to 18 carbon atoms, halo or hydroxy alkyl of 2 to 20 carbon atoms, halo or hydroxy alkenyl of 2 to 20 carbon atoms, cycloalkyl of 5 to 6 carbon atoms, benzyl, phenyl or halophenyl, each R⁗ is alkyl of 1 to 20 carbon atoms, alkenyl of 2 to 18 carbon atoms, halo or hydroxyl alkyl or alkenyl of 2 to 18 carbon atoms, cycloalkyl of 5 to 6 carbon atoms, benzyl, phenyl or halophenyl, x is 1 or 2, y is 1 or 2 and z is 1 or 2, the total of x+y+z is 4, $$Z \text{ is } -S-R_4O\overset{O}{\overset{\|}{C}}R_6S-, -SR_4O\overset{O}{\overset{\|}{C}}R_6\overset{O}{\overset{\|}{C}}R_4S-,$$

$$[[-SR_6\overset{O}{\overset{\|}{C}}R_5\overset{O}{\overset{\|}{C}}R_6S-,]] \quad -SR_6\overset{O}{\overset{\|}{C}}, -SR_6\overset{O}{\overset{\|}{C}}R_{13}\overset{O}{\overset{\|}{C}}RS-$$

$$-O\overset{O}{\overset{\|}{C}}R_5\overset{O}{\overset{\|}{C}}, -SR_4O\overset{O}{\overset{\|}{C}}R_5\overset{O}{\overset{\|}{C}}-O-,$$

$$[[-O\overset{O}{\overset{\|}{C}}R_5\overset{O}{\overset{\|}{C}}OR_6O\overset{O}{\overset{\|}{C}}R_5\overset{O}{\overset{\|}{C}}O-,]] \quad -O\overset{O}{\overset{\|}{C}}R_5\overset{O}{\overset{\|}{C}}OR_4O\overset{O}{\overset{\|}{C}}R_5-\overset{O}{\overset{\|}{C}}O-,$$

$$SR_4O\overset{O}{\overset{\|}{C}}-R_5-\overset{O}{\overset{\|}{C}}-OR_4S-$$

$$\text{or } -O\overset{O}{\overset{\|}{C}}R_9-\overset{O}{\overset{\|}{C}}R_{10}-O\overset{O}{\overset{\|}{C}}R_9\overset{O}{\overset{\|}{C}}O-.$$

where $R_4$ is arylene, —CH=CH—, alkylene of 2 to 10 carbon atoms, $R_5$ is nothing, alkylene of 1 to 8 carbon atoms, phenylene or —CH=CH—, $R_6$ is alkylene of 1 to 10 carbon atoms, —CH=CH— or arlyene, $R_{13}$ is phenylene, alkylene of 2 to 8 carbon atoms or —CH=CH—, $R_9$ is a residue of a dicarboxylic acid from which the two carboxyl groups have been removed, $R_{10}$ is arylene or

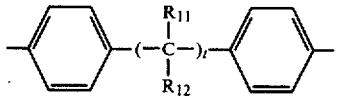

where t is 0 to 1 and $R_{11}$ and $R_{12}$ are H or alkyl, or (2) an overbased compound prepared by reacting a dialkytin oxide of alkystannoic acid with a compound of the formula:

$$R_x\underset{\underset{(A)_y}{|}}{Sn}-(Z)_z-\underset{\underset{(A)_y}{|}}{SnR_x}$$

2. A compound according to claim 1 having formula (1).

3. A compound according to claim 2 wherein x and z are 1 and y is 2.

4. A compound according to claim 3 wherein one A attached to each tin atom is halogen of atomic weight 35 to 127, and the other A is $$-SR'O\overset{O}{\overset{\|}{C}}R''.$$

5. A compound according to claim 3 wherein all of the A groups are $$-SR'O\overset{O}{\overset{\|}{C}}R''.$$

6. A compound according to claim 2 wherein d is 0.

7. A compound according to claim 6 wherein x and z are 1 and y is 2.

8. A compound according to claim 2 wherein, z is 1 and the A groups are $$-SR'O\overset{O}{\overset{\|}{C}}R''$$

or halogen of atomic weight 35 to 127.

9. A compound according to claim 8 wherein Z is $$[[-SR_4O\overset{O}{\overset{\|}{C}}-R_3-\overset{O}{\overset{\|}{C}}OR_4S-.]] \quad SR_4O\overset{O}{\overset{\|}{C}}-R_5-\overset{O}{\overset{\|}{C}}OR_4S-$$

10. A compound according to claim 9 wherein R″ is alkyl or ethylenically unsaturated aliphatic hydrocarbyl.

11. A compound according to claim 10 wherein $R_4$ is alkylene.

12. A compound according to claim 10 wherein $R_4$ is p-phenylene.

13. A compound according to claim 10 wherein $R_4$ is —CH=CH—.

14. A compound according to claim 8 wherein Z is $$-S-R_4OC(=O)R_6S-.$$

15. A compound according to claim 14 wherein $R_4$ and $R_6$ are both alkylene.

16. A compound according to claim 14 wherein $R_4$ and $R_6$ are both —CH=CH—.

17. A compound according to claim 14 wherein $R_4$ and $R_6$ are both

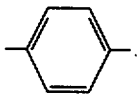

18. A compound according to claim 14 wherein R″ is alkyl or ethylenically unsaturated aliphatic hydrocarbyl.

19. A compound according to claim 8 wherein Z is $$-SR_4OC(=O)R_6COR_4S-.$$

20. A compound according to claim 8 wherein Z is $$-SR_6C(=O)O-.$$

21. A compound according to claim 20 wherein R″ is alkyl or ethylenically unsaturated aliphatic hydrocarbyl.

22. A compound according to claim 8 wherein Z is $$-OC(=O)R_5C(=O)O-.$$

23. A compound according to claim 22 wherein R″ is alkyl or ethylenically unsaturated aliphatic hydrocarbyl.

24. A compound according to claim 23 wherein $R_5$ is nothing or alkylene.

25. A compound according to claim 23 wherein $R_5$ is —CH=CH—.

26. A compound according to claim 23 wherein $R_5$ is phenylene.

27. A compound according to claim 8 wherein Z is $$-SR_4OC(=O)R_5C(=O)-O.$$

28. A compound according to claim 27 wherein R″ is alkyl or ethylenically unsaturated aliphatic hydrocarbyl.

29. A compound according to claim 8 wherein Z is $$[[-OC(=O)R_5COOR_4OC(=O)R_5CO-.]] \quad -OC(=O)R_5COOR_4OC(=O)R_5CO-$$

30. A compound according to claim 29 wherein R″ is alkyl or ethylenically unsaturated aliphatic hydrocarbyl.

31. A compound according to claim 8 wherein Z is $$-SR_4OC(=O)-R_5-C(=O)-C[[R_4S]]-.$$

32. A compound according to claim 31 wherein R″ is alkyl or ethylenically unsaturated aliphatic hydrocarbyl.

33. A compound according to claim 8 wherein Z is $$-S(CH_2)_nOC(=O)CH=CHC(=O)O(CH_2)_n-S-,$$

where n is 2.

[[34. A compound according to claim 33 wherein n is 2.]]

35. [[A compound according to claim 8 wherein Z]] is $$[[-S(CH_2)_nC(=O)OR_5OC(=O)(CH_2)_nS-.]]$$

A sulfur containing organotin compound having the formula

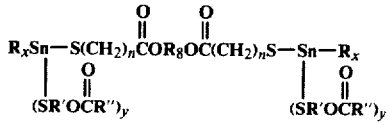

where R is a monovalent alkyl radical of 1 to 8 carbon atoms, each R′ is alkylene of 2 to 10 carbon atoms each R″ is alkyl of 1 to 20 carbon atoms, ethylenically unsaturated aliphatic hydrocarbyl having 1 to 3 ethylenic double bonds and 2 to 19 carbon atoms, halo or hydroxy alkyl of 2 to 19 carbon atoms, halo or hydroxyl alkenyl of 2 to 19 carbon atoms, cycloalkyl of 5 to 6 carbon atoms, benzyl, phenyl, alkylphenyl, halophenyl,

$$R'''C(=O)OR''''$$

where R‴ is alkylene of 2 to 10 carbon atoms, R⁗ is alkyl of 1 to 20 carbon atoms, alkenyl of 2 to 18 carbon atoms, halo of hydroxy alkyl or alkenyl of 2 to 18 carbon atoms, cycloalkyl of 5 to 6 carbon atoms, benzyl, phenyl or halophenyl, x is 1 or 2, y is 1 or 2 and the total of x+y is 3, $R_8$ is alkylene of 2 to 10 carbon atoms or cyclohexane dimethylene, n is 1 or 2 or (2) an overbased compound prepared by reacting a dialkyltin oxide of alkylstannoic acid with a compound of the formula

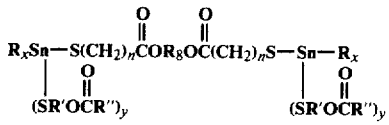

36. A compound according to claim 35 wherein n is 1.

37. A compound according to claim 35 wherein $R_8$ is alkylene of 2 to 10 carbon atoms.

38. A compound according to claim 8 wherein Z is $$-OC(=O)R_9-C(=O)-OR_{10}-OC(=O)R_9C(=O)-O.$$

39. A compound according to claim 38 wherein $R_9$ is $(CH_2)_m$ where m is an integer from 0 to 8.

40. A compound according to claim 38 wherein $R_9$ is —CH=CH—.

41. A compound according to claim 38 wherein $R_9$ is

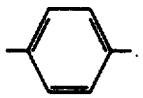

42. A compound according to claim 38 where $R_{10}$ is

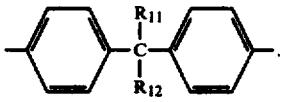

43. A compound according to claim [2] *42* wherein $R_{11}$ and $R_{12}$ are methyl.

44. A compound according to claim 43 wherein $R_9$ is $(CH_2)_m$ where m is an integer of 0 to 8, —CH=CH—or phenylene.

45. A compound according to claim 2 wherein d is 1 and R" is alkyl, ethylenically unsaturated aliphatic hydrocarbyl or monohydroxy substituted monoethylenically unsaturated aliphatic hydrocarbyl.

46. A compound according to claim 45 wherein at least one of the A groups is $$-SR'\overset{O}{\overset{\|}{O}}CR''$$

and the balance of the A groups are $$-SR'\overset{O}{\overset{\|}{O}}CR''$$

or halogen of atomic weight 35 to 127.

47. A compound according to claim 46 wherein all of the A groups are $$-SR'\overset{O}{\overset{\|}{O}}CR''.$$

48. A compound according to claim 46 wherein at least one A group is halogen of atomic weight 35 to 127.

49. A compound according to claim 48 wherein the halogen is chlorine.

50. A compound according to claim 1 which is (2).

51. A compound according to claim 50 wherein R is methyl.

52. A compound according to claim 45 wherein R is methyl.

53. A compound according to claim 2 wherein R is methyl.

54. A halogen-containing polymer composition containing a compound according to claim 1 in an amount effective to heat stabilize the polymer.

55. A composition according to claim 54 wherein the halogen containing polymer is selected from the group consisting of vinyl chloride polymers, chlorinated polyethylene, chlorinated rubber, chlorinated polystyrene, chlorinated polyvinyl chloride and rubber hydrochloride.

* * * * *